US006825205B2

(12) United States Patent
Kyle

(10) Patent No.: US 6,825,205 B2
(45) Date of Patent: Nov. 30, 2004

(54) N-SUBSTITUTED HYDROMORPHONES AND THE USE THEREOF

(75) Inventor: Donald J. Kyle, Newtown, PA (US)

(73) Assignee: Euro-Celtique S.A., Luxembourg (LU)

( * ) Notice: Subject to any disclaimer, the term of this patent is extended or adjusted under 35 U.S.C. 154(b) by 0 days.

(21) Appl. No.: 10/668,326

(22) Filed: Sep. 24, 2003

(65) Prior Publication Data

US 2004/0067973 A1 Apr. 8, 2004

Related U.S. Application Data

(60) Provisional application No. 60/413,254, filed on Sep. 25, 2002.

(51) Int. Cl.[7] ..................... A61K 31/485; C07D 489/00
(52) U.S. Cl. ............................ 514/282; 546/45; 546/44
(58) Field of Search .......................... 514/282; 546/45, 546/44

(56) References Cited

U.S. PATENT DOCUMENTS

| 3,536,809 A | 10/1970 | Applezweig |
| 3,598,123 A | 8/1971 | Zaffaroni |
| 3,845,770 A | 11/1974 | Theeuwes et al. |
| 3,916,899 A | 11/1975 | Theeuwes et al. |
| 4,008,719 A | 2/1977 | Theeuwes et al. |
| 5,059,595 A | 10/1991 | Le Grazie |
| 5,073,543 A | 12/1991 | Marshall et al. |
| 5,120,548 A | 6/1992 | McClelland et al. |
| 5,354,556 A | 10/1994 | Sparks et al. |
| 5,591,767 A | 1/1997 | Mohr et al. |
| 5,639,476 A | 6/1997 | Oshlack et al. |
| 5,674,533 A | 10/1997 | Santus et al. |
| 5,698,155 A | 12/1997 | Grosswald et al. |
| 5,733,566 A | 3/1998 | Lewis |
| 6,294,195 B1 | 9/2001 | Oshlack et al. |

OTHER PUBLICATIONS

Freund, M., and Speyer, E., "Über die Reduktionsprodukte des Thebains," Ber. 53B:2250–2264, Wiley–VCH Verlag GmbH & Co. (1920).
Rapoport, H., et al., "The Preparation of Some Dihydro Ketones in the Morphine Series by Oppenauer Oxidation," J. Org. Chem. 15:1103–1107, American Chemical Society (1950).
Small, L., et al., "The Addition of Organomagnesium Halides to Pseudocodeine Types. II. Preparation of Nuclear Alkylated Morphine Derivatives," J. Am. Chem. Soc. 58:1457–1463, American Chemical Society (1936).
Small, L., et al., "The Addition of Organomagnesium Halides to Pseudocodeine Types. IV. Nuclear–Substituted Morphine Derivatives," J. Org. Chem. 3:204–232, American Chemical Society (1938).

Database CA 'Online!, Chemical Abstracts Service, Columbus, OH, Accession No. 65:47914, Abstract for Seki, I., "Morphine Alkaloids and Related Compounds. XIV. Preparation of 6–aminohydrophenanthrenes from Hofmann Degradation Products of Morphine Alkaloids," Chem. Pharm. Bull. 14:453–461 (1966).
International Search Report for International Application No. PCT/US03/29876, mailed on Mar. 2, 2004, The Hague, Netherlands.
Database CA 'Online!, Chemical Abstracts Service, Columbus OH, Accession No. 1921:7163, Abstract for Freund, M., et al., "Reduction products of thebaine," Ber. 53B:2250–2264, Wiley–VCH Verlag GmbH & Co. (1920).
Baumhaker, Y., and Sarne, Y., "Exposure of NG108–15 Cells to Etorphine Induces an Embedded State of the Opioid Receptor Which Discriminates Between Hydrophilic and Hydrophobic Ligands," Pharmacology Communications 7:149–155, Overseas Publishers Association and Harwood Academic Publishers (1996).
Brent, P.J., "Behavioural Effect of Pretreatment with Opioid Antagonists and Sigma Binding Site Ligands on the Abnormal Motor Response Produced by the Kappa Opioid Agonist U50,488H in Guinea Pigs," Neuropharmacology 32:751–760, Pergamon Press (1993).
Buchwald, H., et al., "Long–term, continuous intravenous heparin administration by an implantable infusion pump in ambulatory patients with recurrent venous thrombosis," Surgery 88:507–516, The C.V. Mosby Company (1980).
During, M.J., et al., "Controlled Release of Dopamine from a Polymeric Brain Implant: In Vivo Characterization," Ann. Neurol. 25:351–356, Little, Brown and Company (1989).

(List continued on next page.)

Primary Examiner—Charanjit S. Aulakh
(74) Attorney, Agent, or Firm—Sterne, Kessler, Goldstein & Fox P.L.L.C.

(57) ABSTRACT

This invention relates to N-substituted hydromorphones of Formula I:

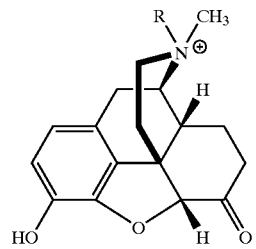

or a pharmaceutically acceptable salt thereof, wherein R is $C_{1-6}$ alkyl. These compounds act as $\mu$ opioid receptor agonists. The invention is also directed to the use of compounds of Formula I for the treatment, prevention or amelioration of both acute and chronic pain.

10 Claims, No Drawings

OTHER PUBLICATIONS

Foss, J.F., "A Review of the Potential Role of Methylnaltrexone in Opioid Bowel Dysfunction," *Am. J. Surg.* 182(*Suppl. To Nov. 2001*):19S–26S, Excerpta Medica, Inc. (Nov. 2001).

Goodson, J.M., "Dental Applications," in *Medical Applications of Controlled Release, vol. II Applications and Evaluation*, Langer, R.S., and Wise, D.L., ed., CRC Press, Inc., Boca Raton, FL, pp. 115–138 (1984).

Griffiths, S.P., et al., "Heterogeneous Enantioselective Hydrogenation Catalysed by Platinum Modified by Some Morphine Alkaloids," in *Catalysis of Organic Reactions*, Herkes, F.E., ed., Marcel Dekker, Inc., New York, NY, pp. 89–100 (1998).

Howard III, M.A., et al., "Intracerebral drug delivery in rats with lesion–induced memory deficits," *J. Neurosurg.* 71:105–112, American Association of Neurological Surgeons (1989).

Hunskaar, S., et al., "Formalin test in mice, a useful technique for evaliating mild analgesics," *J. Neurosci Meth.* 14:69–76, Elsevier Science Publishers B.V. (1985).

Iorio, M.A., and Frigeni, V., "Narcotic agonist/antagonist properties of quaternary diastereoisomers derived from oxymorphone and naloxone," *Eur. J. Med. Chem.–Chim. Ther.* 19:301–303, Editions Scientifiques Elsevier (1984).

Langer, R., "New Methods of Drug Delivery," *Science* 249:1527–1533, American Association for the Advancement of Science (1990).

Langer, R., and Peppas, N., "Chemical and Physical Structure of Polymers as Carriers for Controlled Release of Bioactive Agents: A Review," *J. Macromol. Sci. Rev. Macromol. Chem. Phys.* C23:61–126, Marcel Dekker, Inc. (1983).

Leander, J.D., "A *Kappa* Opioid Effect: Increased Urination in the Rat," *J. Pharmacol. Exp. Ther.* 224:89–94, The American Society for Pharmacology and Experimental Therapeutics (1983).

Levy, R.J., et al., "Inhibition of Calcification of Bioprosthetic Heart Valves by Local Controlled–Release Diphosphonate," *Science* 228:190–192, American Association for the Advancement of Science (1985).

Milne, R.J., et al., "Quaternary naloxone blocks morphine analgesia in spinal but not intact rats," *Neurosci. Lett.* 114:259–264, Elsevier Scientific Publishers Ireland Ltd. (1990).

Murphy, D.B., et al., "Pharmacokinetic profile of epidurally administrated methylnaltrexone, a novel peripheral opioid antagonist in a rabbit model," *Br. J. Anaesth.* 86:120–122, Oxford University Press (Jan. 2001).

Panaerai, A.E., et al., "Opiates Act Centrally on GH and PRL Release," *Endocrinology* 108:2400–2402, The Endocrine Society (1981).

Saudek, C.D., et al., "A Preliminary Trial of the Programmable Implantable Medication System for Insulin Delivery," *N. Engl. J. Med.* 321:574–579, Massachusetts Medical Society (1989).

Sefton, M.V., "Implantable Pumps," *Crit. Rev. Biomed. Eng.* 14:201–240, CRC Press (1987).

Valle, L., et al., "Effects of $\mu$–opioid receptor agonists on intestinal secretion and permeability during acute intestinal inflammation in mice," *Eur. J. Pharmacol.* 389:235–242, Elsevier Science B.V. (2000).

Yuan, C.–S., et al., "Effects of Subcutaneous Methylnaltrexone on Morphine–Induced Peripherally Mediated Side Effects: A Double–Blind Randomized Placebo–Controlled Trial," *J. Pharmacol. Exp. Ther.* 300:118–123, The American Society for Pharmacology and Experimental Therapeutics (Jan. 2002).

N-SUBSTITUTED HYDROMORPHONES AND THE USE THEREOF

BACKGROUND OF THE INVENTION

This application claims the priority benefit under 35 U.S.C. § 119(e) of U.S. Provisional Application No. 60/413,254, filed Sep. 25, 2002, the entirety of which is incorporated by reference herein.

1. Field of the Invention

This invention is in the field of medicinal chemistry. In particular, the invention relates to novel N-substituted hydromorphones.

2. Related Art

The primary location of pain control is in the central nervous system (CNS). The three primary classes of opioid receptors, μ (mu), κ (kappa), and δ (delta), are distributed throughout the CNS and the periphery (Foss, J. F., *The American Journal of Surgery* 182 (Suppl to November 2001):19S–26S (2001)). μ, κ, and δ opioid receptors are functionally coupled to pertussis toxin sensitive heterotrimeric G proteins ($G_i$) to inhibit adenylyl cyclase activity. Activation of these receptors activates $K^+$ currents which increases $K^+$ efflux, i.e., hyperpolarization, thereby reducing voltage-gated $Ca^{2+}$ entry. Hyperpolarization of membrane potential by $K^+$ currents and inhibition of the $Ca^{2+}$ influx prevents neurotransmitter release and pain transmission in varying neuronal pathways. However, the principal receptor involved in pain management is the μ opioid receptor (Foss, J. F., ibid). Other consequences of μ-receptor activation include delays in gastrointestinal transit, respiratory depression, miosis, and feelings of well-being (euphoria) (Foss, J. F., ibid).

Opioids, also known as opioid agonists, are a group of drugs that exhibit opium or morphine-like properties, suppress neuronal activity at the above mentioned opioid receptors. The opioids are widely administered for a variety of medical indications but primarily they are employed as moderate to strong analgesics. Opioid compounds have been reported to have a number of side effects, including constipation, dysphoria, respiratory depresession, dizziness, nausea, and pruritus (Yuan, C.-S. et al., *J. Pharm. Exp. Ther.* 300:118–123 (2002)). CNS-mediated side effects include the abuse potential of opioids. Opioids are also effective as a preanesthetic medication and a cough suppressant, and in treating dyspnea, diarrhea and dysentery.

There have been attempts to selectively antagonize opioid-induced side effects via the use of receptor antagonists such as naloxone or nalmephene. However, the success has been limited because these compounds also reverse analgesia and induce opioid withdrawal (Yuan, C.-S. et al., *J. Pharm. Exp. Ther.* 300:118–123 (2002)). Methylnaltrexone, a quaternary derivative of the pure opioid antagonist naltrexone, has been reported to block undesired side effects of opioid pain medications predominantly mediated by peripherally located receptors, while sparing centrally mediated analgesic effect (Yuan, C.-S. et al., *J. Pharm. Exp. Ther.* 300:118–123 (2002)). It has been reported that methylnaltrexone does not cross the blood-brain barrier in humans (Foss, J. F., *The American Journal of Surgery* 182 (Suppl to November 2001):19S–26S (2001)).

There still exists a need in the art to provide efficient analgesia without CNS-mediated side effects.

SUMMARY OF THE INVENTION

The present invention is related to the discovery that N-alkyl substituted hydromorphones represented by Formula I act as μ opioid receptor agonists, and that they do not penetrate the central nervous system (CNS).

The invention is also related to treating, preventing or ameliorating pain, especially chronic pain, in a mammal in need thereof by administering an effective amount of a compound of Formula I as described herein.

The compounds useful in the present invention have not been heretofor reported. Thus, one aspect of the present invention is directed to the novel N-alkyl substituted hydromorphones of Formula I.

Another aspect of the present invention is directed to the novel compounds of Formula I as μ opioid receptor agonists.

Also, an aspect of the present invention is to provide a pharmaceutical composition useful for treating, preventing or ameliorating pain, containing an effective amount of a compound of Formula I in a mixture with one or more pharmaceutically acceptable carriers or diluents.

Additional embodiments and advantages of the invention will be set forth in part in the description that follows, and in part will be obvious from the description, or may be learned by practice of the invention. The embodiments and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

DETAILED DESCRIPTION OF THE INVENTION

The inventors have found that hydromorphone derivatives of Formula I act as potent μ opioid receptor agonists. Furthermore, it has been found that compounds of Formula I do not cross the blood-brain barrier and, thus, should not have CNS-mediated side effects. Therefore, compounds of Formula I are useful for treating disorders responsive to the excitation of μ opioid receptors in the periphery, especially pain. Since compounds of Formula I do not cross the blood-brain barrier there is no potential for abuse.

The compounds useful in this aspect of the present invention are N-alkyl substituted derivatives of hydromorphone represented by Formula I:

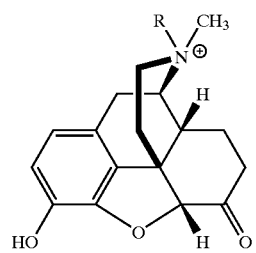

I or a pharmaceutically acceptable salt thereof, wherein:

R is $C_{1-6}$ alkyl.

Useful alkyl groups include straight-chained and branched $C_{1-6}$ alkyl groups, more preferably $C_{1-4}$ alkyl groups. Typical $C_{1-6}$ alkyl groups include methyl, ethyl, propyl, isopropyl, butyl, sec-butyl, tert-butyl, 3-pentyl, and hexyl groups.

R is preferably methyl or ethyl, more preferably methyl.

Since the compounds of Formula I are agonists of peripheral μ opioid receptors, they can be used for treating, preventing or ameliorating pain including acute pain and chronic pain, inflammatory pain, and surgical pain. Acute pain includes, but is not limited to, perioperative pain, postoperative pain, post-traumatic pain, acute disease related pain, and pain related to diagnostic procedures, orthopedic manipulations, and myocardial infarction. Acute pain in the perioperative setting includes pain because of pre-existing disease, the surgical procedure, e.g., associated drains, chest or nasogastric tubes, or complications, or a combination of disease-related and procedure-related sources. Chronic pain includes, but is not limited to, inflammatory pain, postoperative pain, cancer pain, osteoarthritis pain associated with metastatic cancer, trigeminal neuralgia, acute herpetic and postherpetic neuralgia, diabethic neuropathy, causalgia, brachial plexus avulsion, occipital neuralgia, reflex sympathetic dystrophy, fibromyalgia, gout, phantom limb pain, burn pain, and other forms of neuralgia, neuropathic, and idiopathic pain syndromes. In each instance, the methods of the present invention require administering to an animal in need of such treatment an effective amount of a $\mu$ opioid receptor agonist of the present invention, or a pharmaceutically acceptable salt thereof.

Chronic pain or neuropathic pain is a heterogenous disease state with an unclear etiology. In chronic pain, the pain can be mediated by multiple mechanisms. This type of pain generally arises from injury to the peripheral or central nervous tissue. The syndromes include pain associated with spinal cord injury, multiple sclerosis, post-herpetic neuralgia, trigeminal neuralgia, phantom pain, causalgia, and reflex sympathetic dystrophy and lower back pain. The chronic pain is different from acute pain in that patients suffer the abnormal pain sensations that can be described as spontaneous pain, continuous superficial burning and/or deep aching pain. The pain can be evoked by heat-, cold-, and mechano-hyperalgesia or by heat-, cold-, or mechano-allodynia.

Neuropathic pain can be caused by injury or infection of peripheral sensory nerves. It includes, but is not limited to pain from peripheral nerve trauma, herpes virus infection, diabetes mellitus, causalgia, plexus avulsion, neuroma, limb amputation, and vasculitis. Neuropathic pain is also caused by nerve damage from chronic alcoholism, human immunodeficiency virus infection, hypothyroidism, uremia, or vitamin deficiences. Neuropathic pain includes but is not limited to pain caused by nerve injury such as, for example, the pain from which diabetics suffer.

Compounds of Formula I can also be used as cough suppressants, and in treating or ameliorating dyspnea, diarrhea and dysentery.

Exemplary preferred compound that may be employed in this method of invention include, without limitation, N-methylhydromorphone or a pharmaceutically acceptable salt thereof. Advantageously, the pharmaceutically acceptable salt is a halogenide, such as a iodide, a chloride or a bromide salt.

Some of the compounds disclosed herein may contain one or more asymmetric centers and may thus give rise to enantiomers, diastereomers, and other stereoisomeric forms. The present invention is also meant to encompass all such possible forms, as well as their racemic and resolved forms and mixtures thereof. The individual enantiomers may be separated according to methods that are well known to those of ordinary skill in the art.

As used herein, the term "stereoisomers" is a general term for all isomers of individual molecules that differ only in the orientation of their atoms in space. It includes enantiomers and isomers of compounds with more than one chiral center that are not mirror images of one another (diastereomers).

The term "chiral center" refers to a carbon atom to which four different groups are attached.

The term "enantiomer" or "enantiomeric" refers to a molecule that is nonsuperimposeable on its mirror image and hence optically active wherein the enantiomer rotates the plane of polarized light in one direction and its mirror image rotates the plane of polarized light in the opposite direction.

The term "racemic" refers to a mixture of equal parts of enantiomers and which is optically inactive.

The term "resolution" refers to the separation or concentration or depletion of one of the two enantiomeric forms of a molecule.

The invention disclosed is also meant to encompass all pharmaceutically acceptable salts thereof of the disclosed compounds. Examples of pharmaceutically acceptable salts include inorganic and organic salts. The pharmaceutically acceptable salts include, but are not limited to, halogenides, such as chloride, bromide, and iodidide, phosphate, sulphate and the like; organic acid salts such as citrate, lactate, tartrate, maleate, fumarate, mandelate, acetate, dichloroacetate, trifluoroacetate, oxalate, formate and the like; sulfonates such as methanesulfonate, benzenesulfonate, p-toluenesulfonate and the like.

The invention is also directed to a method for treating disorders responsive to the excitation of $\mu$ opioid receptors in animals suffering thereof. Particular preferred embodiments of the N-alkyl substituted hydromorphones for use in method of this invention are represented by previously defined Formula I.

The compounds of this invention may be prepared using methods known to those skilled in the art. For example, compounds of the invention can be prepared by Menschutkin reaction. Accordingly, hydromorphone or a salt thereof is allowed to react in a suitable solvent or a solvent mixture with $R^1X$ wherein $R^1$ is a $C_{1-6}$ alkyl group and X is a halogenide, such as iodide, chloride, or bromide, to form a quaternary hydromorphonium salt. Hydromorphone can be prepared by methods known to those skilled in the art or is commercially available by, e.g., Sigma-Aldrich.

Compounds of the present invention may be tested for their $\mu$ opioid receptor binding activity and their functional profile at $\mu$ opioid receptor by the following in vitro binding assays.

$\mu$ Opioid Receptor Binding Assay

Radioligand dose-displacement assays used 0.2 nM [$^3$H]-diprenorphine (Perkin Elmer, Boston, Mass.; 50.0 Ci/mmol) with 20 $\mu$g membrane protein (recombinant $\mu$ opioid receptor expressed in CHO-K1 cells; Perkin Elmer) in a final volume of 500 $\mu$L binding buffer (10 nM MgCl$_2$, 1 mM EDTA, 5% DMSO, 50 mM Trizma base, pH 7.4). Unlabeled naloxone (Sigma) served as the assay positive control (concentration range $3\times10^{-7}$ to $1\times10^{-13}$ M). All reactions were performed in 96-deep well polypropylene plates for 2 hours at room temperature. Binding reactions were terminated by rapid filtration onto 96-well Unifilter GF/C filter plates (Packard, Meriden, Conn.) presoaked in 0.5% polyethylenimine (Sigma). Harvesting was performed using a 96-well tissue harvester (Brandel) followed by three filtration washes with 500 $\mu$L icecold binding buffer. Filter plates were subsequently dried at 50° C. for 2–3 hours. 50 $\mu$L/well scintillation coctail (BetaScint; Perkin Elmer) was added and plates were counted in a Packard Top-Count for 1 min/well.

Opioid Receptor [$^{35}$S]GTP-$\gamma$-S Binding Functional Assay

Functional [$^{35}$S]GTP-$\gamma$-S binding assays were conducted by sequentially mixing the following reagents in the order shown to yield the indicated final concentrations: 0.026 $\mu g/\mu L$ $\mu$ membrane protein, 10 $\mu g/mL$ saponin, 3 $\mu M$ guanosine 5'-diphosphate (GDP) (Sigma Chemical Co., St. Louis, Mo.), and 0.20 nM [$\gamma$-$^{35}$S]guanosine 5'-($\gamma$-thio)-triphosphate ([$^{35}$S]GTP-$\gamma$-S) (DuPont/New England Nuclear Co., Wilmington, Del.) to binding buffer (100 mM NaCl, 10 mM $MgCl_2$, 20 mM HEPES, pH 7.4) on ice. The prepared membrane solution (190 $\mu L$/well) was transferred to 96-shallow well polypropylene plates containing 10 $\mu L$ of 20× concentrated stock solutions of compound or appropriate control prepared in dimethylsulfoxide (DMSO). Unlabeled [D-Ala$^2$, N-MePhe$^4$, Gly$^5$-ol]enkephalin (DAMGO) (Sigma-Aldrich) served as the assay positive control for the $\mu$ functional assay. Plates were incubated for 30 minutes at room temperature with shaking. Reactions were terminated by rapid filtration onto 96-well Unifilter GF/B filter plates (Packard) using a 96-well tissue harvester (Brandel) and followed by three filtration washes with 200 $\mu L$ ice-cold binding buffer (10 nM $NaH_2PO_4$, 10 mM $Na_2HPO_4$, pH 7.4). Filter plates were subsequently dried at 50° C. for 2–3 hours. 50 $\mu L$/well scintillation coctail (BetaScint, Wallac) was added and plates were counted in a Packard Top-Count for 1 min/well.

Data analysis: Data from both the binding and functional assays were analyzed using the curve fitting functions in GraphPad PRISM™, v. 3.0. Data were expressed as mean±S.E.M. The results from the binding assays are represented as inhibition constants, $K_i$ values (the concentration of a compound that produces half maximal inhibition). The results from the functional assays are respresented as $EC_{50}$ values (the effective concentration a compound that causes 50% of the maximum response).

In vivo Pharmacology

The compounds of the present invention may be tested for in vivo distribution to brains after i.v., p.o. or i.p. injection using, for example, the following test. Sprague Dawley rats were dosed 10 mg/kg i.p. the test compound. The dosing solution was in 25% 2-hydroxypropyl beta-cyclodextrin (HPBCD) and the dosing volume was 5 mL/kg. One hour after administration, the highest possible volume of blood was drawn through cardiac puncture. Plasma was separated from the whole blood by centrifugation and submitted for the analysis. Following the bleeding, the whole brains were harvested, briefly rinsed in cold normal saline and then snap-frozen in liquid nitrogen. Both plasma and brain samples were stored at −70° C. prior to analysis.

For analyzing the plasma samples, calibration curves were prepared by spiking down amounts of analytes into commercially available control rat plasma. 200 $\mu L$ aliquots of standards and study samples were added with 800 $\mu L$ aqueous solution of internal standard (oxycodone) and extracted on the $C_{18}$ solid-phase cartridges (96-well format, 3M) according to the following procedure. The cartridges were activated by applying 500 $\mu L$ methanol followed by 500 $\mu L$ of water. Then the samples were applied and cartridges were washed with 500 $\mu L$ of water and then eluted with 2×500 $\mu L$ of 1% formic acid in methanol followed by 2×500 $\mu L$ of 2% ammonia in methanol. Upon evaporation and reconstitution, the samples were analyzed by LC/MS/MS. For analyzing the brain samples, study samples and control brains were homogenized with water in ratio 1:10 (W:V). Calibration curves were prepared by spiking known amounts of the analytes into control brain homogenates. 500 $\mu L$ aliquots of standards and study samples brain homogenates were added with 500 $\mu L$ aqueous solution of internal standard (oxycodone) and extracted on the $C_{18}$ solid-phase cartridges (96-well format, 3M) according to the procedure described earlier for plasma samples. Upon evaporation and reconstitution, the samples were analyzed by LC/MS/MS.

Analytes and internal standars were chromatographed on Zorbax Extended $C_{18}$ column (4.6×150 mm, 3.5 microns particle size) under water-acetonitrile gradient conditions (specific gradient for each analyte) using procedures well known to those of ordinary skill in the art. The effluents were analyzed by MS/MS. The analytes were registered as "daughter" ions of analytes' molecular ions on the second quadruple of the instrument. The MS/MS conditions were optimized for each individual analyte to achieve maximum selectivity and sensitivity.

The concentrations of the unknown samples were calculated based on the parameters of the corresponding calibration curves. The brain concentrations expressed in "ng per g of tissue" were obtained by multiplying the corresponding homogenate concentrations by factor of 10 (dilution factor during the homogenation step). The brain-to-blood ratio were calculated as the ratio of the corresponding brain (ng/g) and plasma (ng/mL) concentrations for each individual animal and the means and standard deviation were calculated for the groups of three.

The compounds may be tested for their antinociceptive activity in the formalin model as described in Hunskaar, S., O. B. Fasmer, and K. Hole, *J. Neurosci. Methods* 14: 69–76 (1985). Male Swiss Webster NIH mice (20–30 g; Harlan, San Diego, Calif.) were used in all experiments. Food was withdrawn on the day of experiment. Mice were placed in Plexiglass jars for at least 1 hour to accommodate to the environment. Following the accommodation period mice were weighed and given either the compound of interest administered i.p. or p.o., or the appropriate volume of vehicle (10% Tween-80). Fifteen minutes after the i.p. dosing, and 30 minutes after the p.o. dosing mice were injected with formalin (20 $\mu L$ of 5% formaldehyde solution in saline) into the dorsal surface of the right hind paw. Mice were transferred to the Plexiglass jars and monitored for the amount of time spent licking or biting the injected paw. Periods of licking and biting were recorded in 5 minute intervals for 1 hour after the formalin injection. All experiments were done in a blinded manner during the light cycle. The early phase of the formalin response was measured as licking/biting between 0–5 minutes, and the late phase was measured from 15–50 minutes. Differences between vehicle and drug treated groups were analyzed by one-way analysis of variance (ANOVA). A P value $\leq 0.05$ was considered significant. Having activity in blocking the acute and second phase of formalin-induced paw-licking activity, the compounds are considered to be efficacious for acute and chronic pain.

The compounds may be tested for their potential for the treatment of chronic pain (antiallodynic and antihyperalgesic activities) in the Chung model of peripheral neuropathy. Male Sprague-Dawley rats weighing between 200–225 g were anesthetized with halothane (1–3% in a mixture of 70% air and 30% oxygen) and their body temperature controlled during anesthesia through use of a homeothermic blanket. A 2-cm dorsal midline incision was then made at the L5 and L6 level and the para-vertibral muscle groups retracted bilaterally. L5 and L6 spinal nerves were then be exposed, isolated, and tightly ligated with 6-0 silk suture. A sham operation was performed exposing the contralateral L5 and L6 spinal nerves as a negative control.

Tactile Allodynia: Rats were transferred to an elevated testing cage with a wire mesh floor and allowed to acclimate for five to ten minutes. A series of Semmes-Weinstein monofilaments were applied to the plantar surface of the hindpaw to determine the animal's withdrawal threshold. The first filament used possessed a buckling weight of 9.1 gms (0.96 log value) and was applied up to five times to see if it elicited a withdrawal response. If the animal had a withdrawal response then the next lightest filament in the series would be applied up to five times to determine if it could elicit a response. This procedure was repeated with subsequent lesser filaments until there was no response and the lightest filament that elicited a response was recorded. If the animal did not have a withdrawal response from the initial 9.1 gms filament then subsequent filaments of increased weight were applied until a filament elicited a response and this filament was then recorded. For each animal, three measurements were made at every time point to produce an average withdrawal threshold determination. Tests were performed prior to and at 1, 2, 4 and 24 hours post drug administration. Tactile allodynia and mechanical hyperalgesia tests were conducted concurrently.

Mechanical Hyperalgesia: Rats were transferred to an elevated testing cage with a wire mesh floor and allowed to acclimate for five to ten minutes. A slightly blunted needle was touched to the plantar surface of the hindpaw causing a dimpling of the skin without penetrating the skin. Administration of the needle to control paws typically produced a quick flinching reaction, too short to be timed with a stopwatch and arbitrarily given a withdrawal time of 0.5 second. The operated side paw of neuropathic animals exhibited an exaggerated withdrawal response to the blunted needle. A maximum withdrawal time of ten seconds was used as a cutoff time. Withdrawal times for both paws of the animals were measured three times at each time point with a five-minute recovery period between applications. The three measures were used to generate an average withdrawal time for each time point. Tactile allodynia and mechanical hyperalgesia tests were conducted concurrently.

Pharmaceutical compositions within the scope of this invention include all compositions wherein the compounds of the present invention are contained in an amount that is effective to achieve its intended purpose. While individual needs vary, determination of optimal ranges of effective amounts of each component is within the skill of the art. Typically, compounds of Formula I may be administered to mammals, e.g. humans, orally at a dose of from about 0.1 to about 5 mg/kg, or an equivalent amount of the pharmaceutically acceptable salt thereof, of the body weight of the mammal being treated for pain one or more times daily, advantageously every 4 hours. For intramuscular injection, the dose is generally about one-half of the oral dose. The pharmaceutical composition can, if desired, also contain one or more other compatible pharmaceutically active agents.

The unit oral dose may comprise from about 5 mg to about 350 mg, preferably from about 10 mg to about 300 mg, conveniently from about 20 to about 300 mg of a compound of Formula I or a pharmaceutically acceptable salt thereof. The unit dose may be administered one or more times daily, conveniently the unit oral dose is administered every 4 hours.

In addition to administering the compound as a raw chemical, the compounds of the invention may be administered as part of a pharmaceutical preparation containing suitable pharmaceutically acceptable carriers comprising excipients and auxiliaries which facilitate processing of the compounds into preparations which can be used pharmaceutically. Preferably, the preparations, particularly those preparations which can be administered orally and which can be used for the preferred type of administration, such as tablets, dragees, and capsules, and also preparations which can be administered rectally, such as suppositories, as well as suitable solutions for administration by injection or orally, contain from about 0.01 to 99 percent, preferably from about 0.25 to 75 percent of active compound(s), together with the excipient.

The pharmaceutical compositions of the invention may be administered to any animal that may experience the beneficial effects of the compounds of the invention. Foremost among such animals are mammals, e.g., humans, although the invention is not intended to be so limited.

The pharmaceutical compositions of the present invention may be administered by any means that achieve their intended purpose. For example, administration may be by parenteral, subcutaneous, intravenous, intramuscular, intraperitoneal, transdermal, or buccal routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical compositions of the present invention can take the form of solutions, suspensions, emulsion, tablets, pills, pellets, capsules, capsules containing liquids, powders, sustained- or controlled-release formulations, suppositories, emulsions, aerosols, sprays, suspensions, or any other form suitable for use. The pharmaceutical preparations of the present invention are manufactured in a manner which is itself known, for example, by means of conventional mixing, granulating, dragee-making, dissolving, or lyophilizing processes.

Pharmaceutical preparations for oral use can be formulated in accordance with routine procedures as a composition adapted for oral administration, such as by combining the active compounds with solid excipients, optionally grinding the resulting mixture and processing the mixture of granules, after adding suitable auxiliaries, if desired or necessary, to obtain tablets or dragee cores. Compositions for oral delivery can be in the form of tablets, lozenges, aqueous or oily suspensions, granules, powders, emulsions, capsules, syrups, or elixirs, for example. Orally administered compositions can contain one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving compound are also suitable for orally administered compositions. In these latter platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be used.

Suitable excipients are, in particular, fillers such as saccharides, for example lactose or sucrose, mannitol, sodium saccharin or sorbitol, magnesiun carbonate, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings that, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropymethyl-cellulose phthalate, are used. Dye stuffs or pigments may be added to the tablets or dragee coatings, for example, for identification or in order to characterize combinations of active compound doses. Other examples of suitable pharmaceutical excipients are described in *Remington's Pharmaceutical Sciences* pp. 1447–1676 (Alfonso R. Gennaro ed., 19th ed. 1995), incorporated herein by reference. In one embodiment, the excipients are of pharmaceutical grade.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, or liquid paraffin. In addition, stabilizers may be added. The pharmaceutical preparation can be in the form of a capsule as described in, for example, U.S. Pat. No. 5,698,155.

Compounds of Formula I can be delivered in a controlled-release system or a sustained-release system, or a delivery device that are well known to those of ordinary skill in the art. The controlled- or sustained-release systems can be prepared by methods known in the art (see, e.g., Goodson, in Medical Applications of Controlled Release, vol. 2, pp. 115–138 (1984)). Other controlled- or sustained-release systems discussed in the review by Langer, *Science* 249:1527–1533 (1990) can be used. In one embodiment, a pump can be used (Langer, *Science* 249:1527–1533 (1990); Sefton, *CRC Crit. Ref Biomed. Eng.* 14:201 (1987); Buchwald et al., *Surgery* 88:507 (1980); and Saudek et al., *N. Engl. J Med.* 321:574 (1989)). In another embodiment, polymeric materials can be used (see *Medical Applications of Controlled Release* (Langer and Wise eds., 1974); *Controlled Drug Bioavailability, Drug Product Design and Performance* (Smolen and Ball eds., 1984); Ranger and Peppas, *J. Macromol. Sci. Rev. Macromol. Chem.* 23:61 (1983); Levy et al., *Science* 228:190 (1985); During et al., *Ann. Neurol.* 25:351 (1989); and Howard et al., *J. Neurosurg.* 71:105 (1989)). For example, an oral controlled-release formulation comprising one or more compounds of Formula I can be prepared as described in U.S. Pat. No. 6,294,195. Other examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,566, each of which is incorporated herein by reference. Such dosage forms can be used to provide controlled- or sustained-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled- or sustained-release formulations known to those of ordinary skill in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled- or sustained-release.

Controlled- or sustained-release compositions can initially release an amount of a compound of the present invention that promptly produces the desired therapeutic or prophylactic effect, and gradually and continually release other amounts of the compound of the present invention to maintain this level of therapeutic or prophylactic effect over an extended period of time. To maintain a constant level of the compound of the present invention in the body, the compound can be released from the dosage form at a rate that will replace the amount of the compound being metabolized and excreted from the body. Controlled- or sustained-release of an active ingredient can be stimulated by various conditions, including but not limited to, changes in pH, changes in temperature, concentration or availability of enzymes, concentration or availability of water, or other physiological conditions or compounds.

Possible pharmaceutical preparations, which can be used rectally, include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400). Aqueous injection suspensions may contain substances which increase the viscosity of the suspension, and include, for example, sodium carboxymethyl cellulose, sorbitol, and/or dextran. Optionally, the suspension may also contain stabilizers.

The following examples are illustrative, but not limiting, of the method and compositions of the present invention. Other suitable modifications and adaptations of the variety of conditions and parameters normally encountered in clinical therapy and which are obvious to those skilled in the art are within the spirit and scope of the invention.

EXAMPLE 1

N-methylhydromorphonium iodide
(Hydromorphone methiodide)

Hydromorphone hydrochloride (1.9 g, 5.9 mmol) was dissolved in 50 mL of water. To this solution, 50 mL of 20% isopropanol/chloroform was added and the resulting biphasic mixture was made basic (pH 8) with 2M aqueous ammonia. The layers were separated and the aqueous phase was extracted with three more 30 mL fractions of 20% isopropanol/chloroform. The organic phases were combined, washed with saturated sodium chloride, filtered through 1 PS paper, and the solvent was removed on a rotatory evaporator (1.9 g). The residue was dissolved in acetone (10 mL) and crystals began to form. Methyl iodide (2 mL, 32 mmol) was added to this mixture along with 5 mL of acetonitrile. The reaction mixture was stirred at room temperature for 3 hours after which time TLC analysis (mobile phase: 15% triethylamine, 15% methanol, 70% ethyl acetate, silica gel) showed that starting material ($R_f$= 0.14) was no longer present. HPLC analysis showed 54%, 3.2 min (iodide ion), 44%, 4.25 min (product), and 1%, 5.2 min (hydromorphone). The reaction mixture was diluted with 10 mL of acetone and filtered. The filter cake was washed with 3 more 5 mL fractions of acetone and air dried to give 2.4 g of hydromorphone methiodide (88% yield). The yield was not optimized. The product was dried over night under high vacuum. HPLC anal. 54%, 3.2 min (iodide ion), 44%, 4.25 min (product), and 1%, 5.2 min (hydromorphone).

The HPLC conditions were as follows: Alltech Ailtima $C_{18}$, 5μ, 4.6×250 mm column; mobile phase 65:30:5 water:Al:methanol; 254 and 220 nm monitoring wavelenghts. Al=700 mL of water, 300 mL of methanol, 3 mL of triethylamine, and enough phosphoric acid to give a pH of 3.4.

EXAMPLE 2

Evaluation of N-methylhydromorphone in in vitro and in vivo assays

N-methylhydromorphone was tested for its μ opioid receptor binding activity and its functional profile at μ opioid receptor as described above. N-methylhydromorphone was also tested for in vivo distribution to brains using the assay described above. The results of N-methylhydromorphone and other compounds in these tests are represented in Table 1.

TABLE 1

Evaluation of the Tested Compounds as Agonists of μ Opioid Receptor in vitro and in vivo Assay and the Penetration of the Blood-Brain Barrier

| Compound name | μ $K_i$/μM | $EC_{50}$/nM | GTP-γ-S Activity/ Efficacy % DAMGO | Brain/ Blood |
|---|---|---|---|---|
| N-methyl-hydromorphone | 90 ± 28 | 817 ± 83 | 29 ± 1 | 0.02 ± 0.01 |
| Hydromorphone | 0.46 ± 0.08 | 31 ± 2 | 46 ± 4 | 0.33 ± 0.05 |
| Morphine | 1.7 ± 0.07 | 118 ± 28 | 56 ± 4 | 0.42 ± 0.13 |
| Oxycodone | 20 ± 4 | 2537 ± 310 | 46 ± 5 | 2.51 ± 0.51 |

The results of the tests show that N-methylhydromorphone has μ potency and efficacy similar to oxycodone and hydromorphone, but it does not penetrate the CNS.

Having now fully described this invention, it will be understood by those of ordinary skill in the art that the same can be performed within a wide and equivalent range of conditions, formulations and other parameters without affecting the scope of the invention or any embodiment thereof.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

All patents and publications cited herein are fully incorporated by reference herein in their entirety.

What is claimed is:

1. A compound having the Formula I:

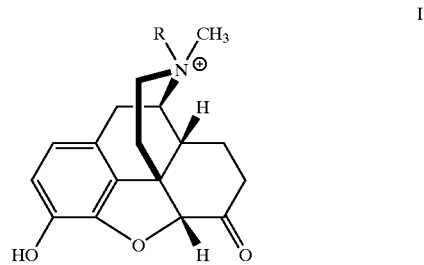

or a pharmaceutically acceptable salt thereof, wherein:
R is $C_{1-6}$ alkyl.

2. The compound of claim 1, wherein R is $C_{1-4}$ alkyl.

3. The compound of claim 2, wherein R is methyl or ethyl.

4. The compound of claim 1, wherein said compound is N-methylhydromorphone or a pharmaceutically acceptable salt thereof.

5. The compound of claim 4, wherein said compound is hydromorphone methiodide.

6. A pharmaceutical composition, comprising one or more compounds as claimed in claim 1, and a pharmaceutically acceptable carrier or diluent.

7. The composition of claim 6, comprising from about 5 mg to about 350 mg of said one or more compounds.

8. A method of treating pain in a mammal suffering therefrom, comprising administering to a mammal in need of such treatment an effective amount of a compound as claimed in claim 1.

9. The method of claim 8, wherein the method is for treating chronic pain.

10. The method of claim 8 or claim 9, comprising administering the compound orally at a dose of about 0.1 to about 5 mg/kg, or an equivalent amount of the pharmaceutically acceptable salt thereof, of the body weight of the mammal being treated every 4 hours.

\* \* \* \* \*